United States Patent
Leaym et al.

(10) Patent No.: US 7,816,479 B2
(45) Date of Patent: Oct. 19, 2010

(54) POLYOXYALKYLENE-ALKYL FUNCTIONAL SILOXANE RESINS AND AQUEOUS COMPOSITIONS THEREOF

(75) Inventors: Tina Marie Leaym, Saginaw, MI (US); Shaow Burn Lin, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 278 days.

(21) Appl. No.: 11/795,186

(22) PCT Filed: Jan. 19, 2006

(86) PCT No.: PCT/US2006/001818

§ 371 (c)(1),
(2), (4) Date: Jul. 12, 2007

(87) PCT Pub. No.: WO2006/091295

PCT Pub. Date: Aug. 31, 2006

(65) Prior Publication Data

US 2008/0175912 A1 Jul. 24, 2008

Related U.S. Application Data

(60) Provisional application No. 60/655,052, filed on Feb. 22, 2005.

(51) Int. Cl.
*B01F 3/08* (2006.01)

(52) U.S. Cl. .............................. 528/25; 528/31; 516/55; 516/76

(58) Field of Classification Search ....................... None
See application file for complete search history.

(56) References Cited

U.S. PATENT DOCUMENTS

| | | | |
|---|---|---|---|
| 5,364,633 A | 11/1994 | Hill et al. | |
| 5,411,744 A | 5/1995 | Hill et al. | |
| 5,484,867 A | 1/1996 | Lichtenhan et al. | |
| 5,919,487 A | 7/1999 | Simonnet et al. | |
| 5,958,448 A | 9/1999 | Ekeland et al. | |
| 6,168,782 B1 | 1/2001 | Lin et al. | |
| 2009/0030162 A1* | 1/2009 | Mueh et al. | 525/477 |

FOREIGN PATENT DOCUMENTS

| | | | |
|---|---|---|---|
| JP | 11-255888 | | 9/1999 |
| JP | 2001-213963 | * | 8/2001 |
| WO | WO 03/101412 A2 | | 12/2003 |
| WO | WO 2004/050045 A1 | | 6/2004 |

OTHER PUBLICATIONS

Machine translation of JP 2001-213963.*
machine translation of JP 2001-213963 (Aug. 2001).*

* cited by examiner

*Primary Examiner*—Marc S Zimmer
(74) *Attorney, Agent, or Firm*—Patricia M. Scaduto; Alan Zombeck

(57) ABSTRACT

Siloxane resins containing both polyoxyalkylene M siloxy units and alkyl functional M and T siloxy units and aqueous compositions thereof are disclosed. The aqueous compositions contain dispersed particles stabilized by the siloxane resin, and are useful for the entrapment and delivery of various personal, household, and medical care actives.

18 Claims, 1 Drawing Sheet

MM'T$^{Pr}$ – PEO Vesicle Dispersion
(Example 5B: made via IPA / water, then IPA stripped)

US 7,816,479 B2

POLYOXYALKYLENE-ALKYL FUNCTIONAL SILOXANE RESINS AND AQUEOUS COMPOSITIONS THEREOF

CROSS REFERENCE TO RELATED APPLICATIONS

This application is a U.S. national stage filing under 35 U.S.C. §371 of PCT Application No. PCT/US2006/001818 filed on 19 Jan. 2006, currently pending, which claims the benefit of U.S. Provisional Patent Application No. 60/655,052 filed 22 Feb. 2005 under 35 U.S.C. §119 (e). PCT Application No. PCT/US2006/001818 and U.S. Provisional Patent Application No. 60/655,052 are hereby incorporated by reference.

TECHNICAL FIELD

This invention relates to siloxane resins containing both polyoxyalkylene and alkyl functional siloxy units and aqueous compositions thereof. The aqueous compositions contain dispersed particles stabilized by the siloxane resin, and are useful for the entrapment and delivery of various personal, household, and medical care actives.

BACKGROUND

Long-standing needs in the field of cosmetic and drug formulation/delivery field are to identify vesicle compositions that form and entrap actives easily, are stable under various chemical and mechanical stresses, and yet are able to deliver the actives in a controlled manner under desired conditions. Vesicles derived from silicone surfactants, and more particularly silicone polyether surfactants, are of interest because of additional inherent benefits that this class of surfactants possesses vs. other types. For example, silicone polyether surfactants often have improved aesthetics in personal care formulations.

The aggregation behavior of certain silicone polyethers has been taught along with their ability to form vesicles. For example, U.S. Pat. Nos. 5,364,633 and 5,411,744 by Hill teaches the self-assembly of silicone vesicles in aqueous dispersions of certain silicone polyethers.

U.S. Pat. No. 5,958,448 teaches a method of entrapping a water-soluble substance in vesicles formed from a surface active siloxane carried out by dissolving the substance to be entrapped in water, adding the surface active siloxane, mildly agitating the mixture, and removing excess water and substance. Water-insoluble substances are entrapped in the vesicles by dissolving the substance to be entrapped in the surface active siloxane, and mildly agitating the substance and the siloxane. The surface active siloxanes consist essentially of tetravalent $SiO_2$, and monovalent $R_3SiO_{1/2}$ and $R'R_2SiO_{1/2}$ units. The ratio of monovalent units to tetravalent units is from 0.4/1 to 2/1, and from 40 to 90% of all monovalent units are $R'R_2SiO_{1/2}$ units. R is a monovalent hydrocarbon group with up to eight carbon atoms, and R' is a polyoxyalkylene group.

PCT application US03/38455 by Lin teaches the entrapment of various oils in certain silicone vesicles and their use in various personal care formulations.

The present inventors have discovered certain siloxane resins containing both polyoxyalkylene functional "M" siloxy units and alkyl functional "T" siloxy units form stable dispersions in water, and in particular vesicle compositions. The aqueous compositions containing the dispersed particles or vesicles formed from the siloxane resins of the present invention are useful for the entrapment and delivery of various personal, household, and medical care active materials.

SUMMARY

This invention relates to a siloxane resin comprising at least 80 mole % of siloxy units having the formula;

$(R^1{}_2R'SiO_{1/2})_x(R''SiO_{3/2})_y$, wherein x and y have a value of 0.1 to 0.95,
$R^1$ is an alkyl or aryl group having from 1 to 8 carbon atoms,
R' is a monovalent polyoxyalkylene group,
R" is a monovalent hydrocarbon group having 2 to 8 carbon atoms.

The invention also relates to aqueous dispersions of the siloxane resin, including vesicle compositions comprising the siloxane resin. The invention further relates to methods for preparing aqueous dispersions and vesicle compositions of the siloxane resin. The invention yet further relates to personal, household, or medical care compositions containing the aqueous compositions of the siloxane resin.

DETAILED DESCRIPTION

Figure 1:
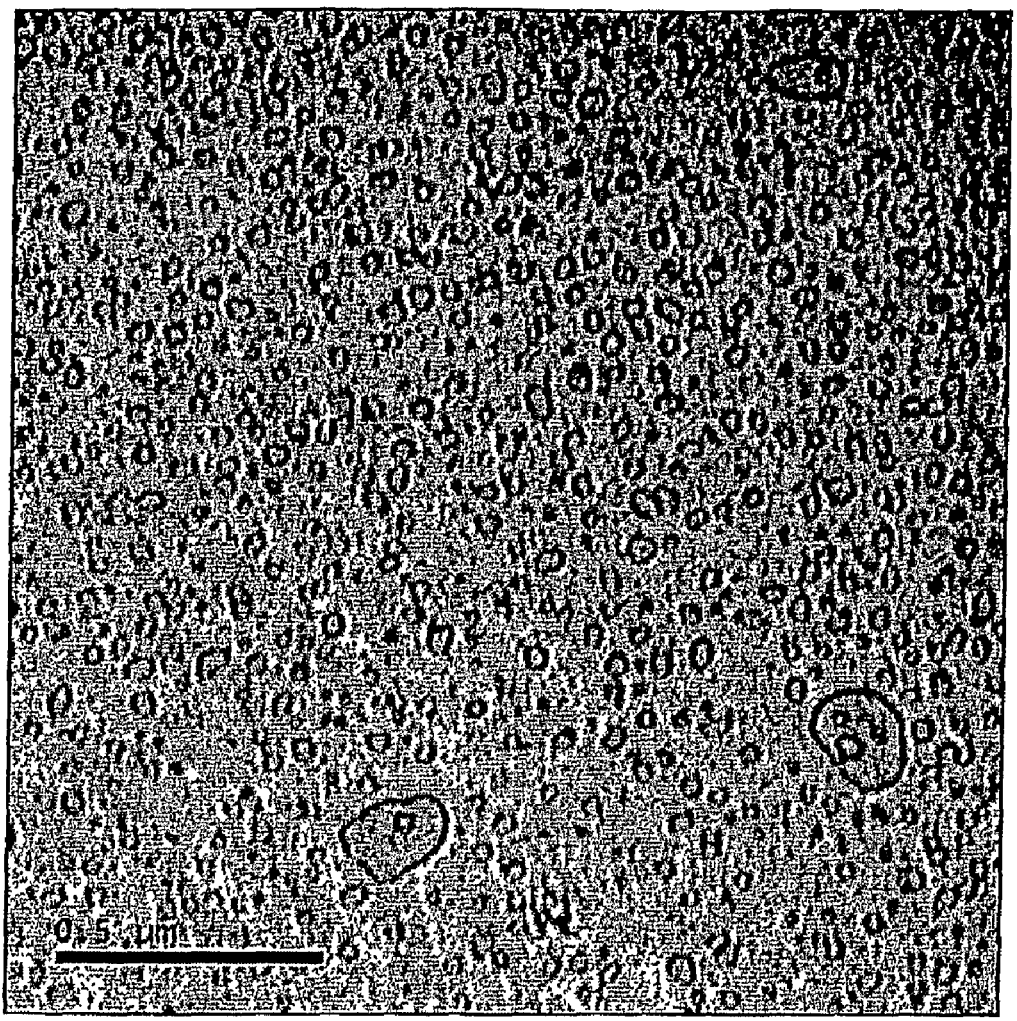
FIG. 1 shows a Cryo-TEM image for the top layer of Example 5B dispersion of the $M_{0.135}M'_{0.035}T^{Pr}{}_{0.82}$-PEO resin.

The siloxane resin of the present invention comprises at least 80 mole % of siloxy units having the formula (Formula I);

$(R^1{}_2R'SiO_{1/2})_x(R''SiO_{3/2})_y$, wherein x and y have a value of 0.1 to 0.95,
$R^1$ is an alkyl or aryl group having from 1 to 8 carbon atoms,
R' is a monovalent polyoxyalkylene group,
R" is a monovalent hydrocarbon group having 2 to 8 carbon atoms.

As used herein, x and y represent the mole fraction of $(R^1{}_2R'SiO_{1/2})$ and $(R'' SiO_{3/2})$ siloxy units (i.e. polyoxyalkylene functional M units and alkyl functional T units respectively) relative to each other present in the siloxane resin. Thus, the mole fraction of $(R^1{}_2R'SiO_{1/2})$, and $(R''SiO_{3/2})_y$ siloxy units each can independently vary from 0.1 to 0.95. However, the combination of $(R^1{}_2R'SiO_{1/2})$ and $(R''SiO_{3/2})$ siloxy units present in the siloxane resin must total at least 80 mole %, alternatively 90 mole %, or alternatively 95 mole % of all siloxy units in the overall formula for the siloxane resin.

R' is a monovalent polyoxyalkylene group. Polyoxyalkylenes are well known in the art and are commonly referred to as "polyethers". The polyoxyalkylene group R' in Formula I may have the formula $—R^4O(C_nH_{2n}O)_zR^5$, wherein n is from 2 to 4 inclusive, z is greater than 4,
$R^4$ is a divalent hydrocarbon containing 2 to 8 carbon atoms,
$R^5$ is hydrogen, an acetyl group, or a monovalent hydrocarbon containing 1 to 8 carbons.

The polyoxyalkylene group of Formula I comprises polyoxyalkylene units represented by the formula $(C_nH_{2n}O)_z$ wherein n is from 2 to 4 inclusive, and z is greater than 4, alternatively z can range from 5 to 30, or alternatively from 5 to 24. The polyoxyalkylene group may comprise oxyethylene units —$C_2H_4O$—, oxypropylene units —$C_3H_6O$—, oxybutylene units —$C_4H_8O$—, or any mixtures thereof. Typically, the polyoxyalkylene block comprises oxyethylene units —$C_2H_4O$—.

At least one end of the polyoxyalkylene group in Formula I is linked to a siloxy unit of the siloxane resin by a divalent organic group, designated $R^4$. The divalent organic groups of $R^4$ may be independently selected from divalent hydrocarbons containing 2 to 30 carbons and divalent organofunctional hydrocarbons containing 2 to 30 carbons. Representative, non-limiting examples of such divalent hydrocarbon groups include; ethylene, propylene, butylene, pentylene, hexylene, heptylene, octylene, and the like. Representative, non-limiting examples of such divalent organofunctional hydrocarbons groups include acrylate and methacrylate. Typically, $R^4$ is propylene, (—$CH_2CH_2CH_2$—).

The terminal end of the R' polyoxyalkylene group of Formula I is represented by $R^5$ and may be selected from hydrogen, an acetyl group ($CH_3C(O)$—), or a monovalent hydrocarbon group containing 1 to 8 carbon atoms. Typically, $R^5$ is hydrogen.

R" is a monovalent hydrocarbon group having 2 to 8 carbon atoms and is illustrated by an ethyl, propyl, butyl, pentyl, hexyl, heptyl, or octyl group. Typically, R" is propyl.

The siloxane resins can contain additional siloxy units such as (i) $(R^1_3SiO_{1/2})_a$, (ii) $(R^2_2SiO_{2/2})_b$, (iii) $(R^3SiO_{3/2})_c$, or (iv) $(SiO_{4/2})_d$ units which are commonly known in the art, and also used herein, as M, D, T, and Q units respectively. The amount of each unit present in the siloxane resin can be expressed as a mole fraction of the total number of moles of all siloxy units present in the alkyl-phenyl silsesquioxane resin. Thus, the siloxane resin of the present invention may comprise the units:

$(R^1_3SiO_{1/2})_a$ (i)

$(R^2_2SiO_{2/2})_b$ (ii)

$(R^3SiO_{3/2})_c$, (iii)

$(SiO_{4/2})_d$, (iv)

$(R^1_2R'SiO_{1/2})_x$ and (v)

$(R"SiO_{3/2})_y$, (vi)

wherein
  $R^1$, $R^2$, and $R^3$ are independently an alkyl or aryl group having from 1 to 8 carbon atoms
  R' is a monovalent polyoxyalkylene group,
  R" is a monovalent hydrocarbon group having 2 to 8 carbon atoms
  a, b, c, and d have value of zero to 0.4,
  x and y have a value of 0.1 to 0.95,
  with the provisos;
    the value of x+y is equal to or greater than 0.80,
    and the value of a+b+c+d+x+y=1.

The $R^1$, $R^2$, and $R^3$ in the units of the siloxane resin are independently an alkyl or aryl group having from 1 to 8 carbon atoms. The alkyl groups are illustrated by methyl, ethyl, propyl, butyl, pentyl, hexyl, and octyl. The aryl groups are illustrated by phenyl, naphthyl, benzyl, tolyl, xylyl, xenyl, methylphenyl, 2-phenylethyl, and 2-phenyl-2-methylethyl, with the aryl group typically being phenyl.

The siloxane resin of this invention are illustrated by a siloxane resin comprising the units;

$(R^1_2R'SiO_{1/2})$, $(CH_3CH_2CH_2SiO_{3/2})_y$, a siloxane resin comprising the units;

$(R^1_2R'SiO_{1/2})_x$ $(CH_3CH_2CH_2SiO_{3/2})_y$ $((CH_3)_3SiO_{1/2})_a$, a siloxane resin comprising the units;

$(R^1_2R'SiO_{1/2})_x$ $(CH_3CH_2CH_2SiO_{3/2})_y$ $((CH_3)_2SiO_{2/2})_b$, a siloxane resin comprising the units;

$(R^1_2R'SiO_{1/2})_x$ $(CH_3CH_2CH_2SiO_{3/2})_y$ $((CH_3)SiO_{3/2})_b$, a siloxane resin comprising the units;

$(R^1_2R'SiO_{1/2})_x$ $(CH_3CH_2CH_2SiO_{3/2})_y$ $(SiO_{4/2})_d$ a siloxane resin comprising the units;

$(R^1_2R'SiO_{1/2})_x$ $(CH_3CH_2CH_2SiO_{3/2})_y$ $((CH_3)_3SiO_{1/2})_a$, $(SiO_{4/2})_d$ a siloxane resin comprising the units;

$(R^1_2R'SiO_{1/2})_x$ $(CH_3CH_2CH_2SiO_{3/2})_y$ $((CH_3)_3SiO_{1/2})_a$, $((CH_3)SiO_{3/2})_c$, a siloxane resin comprising the units;

$(R^1_2R'SiO_{1/2})_x$ $(CH_3CH_2CH_2SiO_{3/2})_y$ $((CH_3)_3SiO_{1/2})_a$, $((CH_3)_2SiO_{2/2})_b$, a siloxane resin comprising the units;

$(R^1_2R'SiO_{1/2})_x$ $(CH_3CH_2CH_2SiO_{3/2})_y$ $((CH_3)_2SiO_{2/2})_b$, $((CH_3)SiO_{3/2})_c$, a siloxane resin comprising the units;

$(R^1{}_2R'SiO_{1/2})_x$ $(CH_3CH_2CH_2SiO_{3/2})_y$ $((CH_3)_2SiO_{2/2})_b$, $(SiO_{4/2})_d$ a siloxane resin comprising the units;

$(R^1{}_2R'SiO_{1/2})_x$ $(CH_3CH_2CH_2SiO_{3/2})_y$ $((CH_3)SiO_{3/2})_c$, $(SiO_{4/2})_d$ a siloxane resin comprising the units;

$(R^1{}_2R'SiO_{1/2})_x$ $(CH_3CH_2CH_2SiO_{3/2})_y$ $((CH_3)_3SiO_{1/2})_a$, $((CH_3)_2SiO_{2/2})_b$, $((CH_3)SiO_{3/2})_c$, and $(SiO_{4/2})_d$ wherein
$R^1$, $R^2$, and $R^3$ are independently an alkyl or aryl group having from 1 to 8 carbon atoms
R' is a monovalent polyoxyalkylene group,
a, b, c, and d have value of zero to 0.4,
x and y have a value of 0.1 to 0.95,
with the provisos;
the value of x+y is equal to or greater than 0.80,
and the value of a+b+c+d+x+y=1.

and R is equal to an alkyl group having from 1 to 8 carbon atoms, an aryl group, a carbinol group, or an amino group.

Typically the polyoxyalkylene group R' has the formula —$(CH_2)_3O(CH_2CH_2O)_zH$, where z is greater than 4, alternatively z can range from 5 to 30, or alternatively from 5 to 24.

In all the formulas illustrated above, the R' polyoxyalkylene group is designated as being on the M siloxy unit. In another embodiment of the present invention, the R' group can be on either a D or T siloxy unit.

The siloxane resins of the present invention can be prepared by any method known in the art for preparing polyoxyalkylene functional siloxane resins, but typically are prepared by reacting a SiH functional siloxane comprising the $(R^1{}_2HSiO_{1/2})_x$ and $(R''SiO_{3/2})_y$ Siloxy units, where $R^1$, R'', x and y are as defined above, with an alkenyl terminated polyoxyalkylene via hydrosilylation reaction techniques. Such hydrosilylation reactions and techniques are well known in the art and are often catalyzed with a platinum compound. The SiH functional siloxane comprising $(R^1{}_2HSiO_{1/2})_x$ and $(R''SiO_{3/2})_y$ siloxy units may also contain additional M, D, T, or Q siloxane units, providing the amount of each present provides a siloxane resin that is compositionally within that described for Formula I above.

The present invention further provides an aqueous composition having dispersed particles wherein the dispersed particles comprise the siloxane resin as shown in Formula I and have an average particle size of less 10 micrometers. The aqueous compositions of the present invention comprise a hydrophobic phase dispersed as discrete particles in a water continuous phase. The hydrophobic phase particles are stabilized in the aqueous compositions by presence of the siloxane resin, as described above. The dispersed hydrophobic phase particles have an average particle size that is less than 10 micrometers, alternatively less than 5 micrometers, or alternatively less than 1 micrometers. "Average particle size" is the accepted meaning in the emulsion art, and can be determined for example using a particle size analyzer such as a Nanotrac 150.

The aqueous compositions may be prepared by any process known in the art for preparing aqueous dispersions or emulsions, and in particular oil/water emulsions. These include stirring, blending, homogenizing, sonalating, and extrusion techniques in either a batch, semi-continuous, or continuous process.

Typically, the aqueous compositions are prepared by a process comprising;

I) mixing,
A) a siloxane resin comprising at least 80 mole % of siloxy units having the formula;

$(R^1{}_2R'SiO_{1/2})_x(R''SiO_{3/2})_y$, wherein x and y have a value of 0.1 to 0.95,
$R^1$ is an alkyl or aryl group having from 1 to 8 carbon atoms,
R' is a monovalent polyoxyalkylene group,
R'' is a monovalent hydrocarbon group having 2 to 8 carbon atoms.
B) optionally, a water miscible volatile solvent,
C) optionally, an organic or silicone oil, with water to form an aqueous dispersion of the siloxane resin, II) optionally, removing the water miscible volatile solvent from the aqueous dispersion.

The siloxane resin component A), is the same as described above as Formula 1. Optional component B) is a water-miscible volatile solvent. As used herein "water-miscible" means the solvent forms a dispersion with water at room temperature for at least several hours. "Volatile" means the solvent has a higher vapor pressure than water at various temperatures. As such, when the aqueous dispersion of the organopolysiloxane and solvent are subjected to conditions to remove the solvent, such as heating the dispersion under reduced pressures, the solvent is primarily removed first, allowing all or most of the water to remain in the composition.

Suitable water-miscible volatile solvents for vesicle dispersion preparation include organic solvents such as alcohols, ethers, glycols, esters, acids, halogenated hydrocarbons, diols. The organic solvents should be miscible with water at the proportion and lower in order to effectively disperse silicones and maintain stable and uniform dispersion overtime. For the purpose of illustration, water-miscible alcohols include method, ethanol, propanol, isopropanol, butanol, and higher hydrocarbon alcohols; ethers include gylcol ethers, methyl-ethyl ether, methyl isobutyl ether (MIBK), etc; glycols include propylene glycols, esters include esters of triglycerol, the esterification products of acid and alcohol; halogenated hydrocarbons include chloroform. Typically water-miscible organic solvents are solvents with relatively low boiling points (<100° C.) or high evaporation rate, so they may be removed under vacuum with ease. The most preferred water-miscible organic solvents for this invention are volatile alcohols including methanol, ethanol, isopropanol, and propanol. These alcohols can be removed from aqueous mixtures containing silicone vesicle dispersions via vacuum stripping at ambient temperature.

Step I) as described above can also comprise component C) a silicone or organic oil. The silicone can be any organopolysiloxane having the general formula $R_iSiO_{(4-i)/2}$ in which i has an average value of one to three and R is a monovalent organic group. The organopolysiloxane can be cyclic, linear, branched, and mixtures thereof.

In one embodiment, the silicone selected as component C) is a volatile methyl siloxane (VMS) which includes low molecular weight linear and cyclic volatile methyl siloxanes. Volatile methyl siloxanes conforming to the CTFA definition of cyclomethicones are considered to be within the definition of low molecular weight siloxane.

Linear VMS have the formula $(CH_3)_3SiO\{(CH_3)_2SiO\}_fSi(CH_3)_3$. The value of f is 0-7. Cyclic VMS have the formula $\{(CH_3)_2SiO\}_g$. The value of g is 3-6. Preferably, these volatile methyl siloxanes have a molecular weight of less than 1,000; a boiling point less than 250° C.; and a viscosity of 0.65 to 5.0 centistoke (mm$^2$/s), generally not greater than 5.0 centistoke (mm$^2$/s).

Representative linear volatile methyl siloxanes are hexamethyldisiloxane (MM) with a boiling point of 100° C., viscosity of 0.65 mm$^2$/s, and formula $Me_3SiOSiMe_3$; octamethyltrisiloxane (MDM) with a boiling point of 152° C., viscosity of 1.04 mm$^2$/s, and formula $Me_3SiOMe_2SiOSiMe_3$; decamethyltetrasiloxane (MD$_2$M) with a boiling point of 194° C., viscosity of 1.53 mm$^2$/s, and formula $Me_3SiO(Me_2SiO)_2SiMe_3$; dodecamethylpentasiloxane (MD$_3$M) with a boiling point of 229° C., viscosity of 2.06 mm$^2$/s, and formula $Me_3SiO(Me_2SiO)_3SiMe_3$; tetradecamethylhexasiloxane (MD$_4$M) with a boiling point of 245° C., viscosity of 2.63 mm$^2$/s, and formula $Me_3SiO(Me_2SiO)_4SiMe_3$; and hexadecamethylheptasiloxane (MD$_5$M) with a boiling point of 270° C., viscosity of 3.24 mm$^2$/s, and formula $Me_3SiO(Me_2SiO)_5SiMe_3$.

Representative cyclic volatile methyl siloxanes are hexamethylcyclotrisiloxane (D$_3$), a solid with a boiling point of 134° C., a molecular weight of 223, and formula $\{(Me_2)SiO\}_3$; octamethylcyclotetrasiloxane (D$_4$) with a boiling point of 176° C., viscosity of 2.3 mm$^2$/s, a molecular weight of 297, and formula $\{(Me_2)SiO\}_4$; decamethylcyclopentasiloxane (D$_5$) with a boiling point of 210° C., viscosity of 3.87 mm$^2$/s, a molecular weight of 371, and formula $\{(Me_2)SiO\}_5$; and dodecamethylcyclohexasiloxane (D$_6$) with a boiling point of 245° C., viscosity of 6.62 mm$^2$/s, a molecular weight of 445, and formula $\{(Me_2)SiO\}_6$.

The silicone selected as component C) can be any polydiorganosiloxane fluid, gum, or mixtures thereof. If the polyorganosiloxane has a molecular weight equal to or greater than 1000, it can be blended with the volatile methyl siloxanes described above. The polydiorganosiloxane gums suitable for the present invention are essentially composed of dimethylsiloxane units with the other units being represented by monomethylsiloxane, trimethylsiloxane, methylvinylsiloxane, methylethylsiloxane, diethylsiloxane, methylphenylsiloxane, diphenylsiloxane, ethylphenylsiloxane, vinylethylsiloxane, phenylvinylsiloxane, 3,3,3-trifluoropropylmethylsiloxane, dimethylphenylsiloxane, methylphenylvinylsiloxane, dimethylethylsiloxane, 3,3,3-trifluoropropyldimethylsiloxane, mono-3,3,3-trifluoropropylsiloxane, aminoalkylsiloxane, monophenylsiloxane, monovinylsiloxane and the like.

When component C) is an organic oil, it may be selected from any organic oil known in the art suitable for use in the preparation of personal, household, or healthcare formulations. Suitable organic oils include, but are not limited to, natural oils such as coconut oil; hydrocarbons such as mineral oil and hydrogenated polyisobutene; fatty alcohols such as octyldodecanol; esters such as C12-C15 alkyl benzoate; diesters such as propylene dipelarganate; and triesters, such as glyceryl trioctanoate. The organic oil components can also be mixture of low viscosity and high viscosity oils. Suitable low viscosity oils have a viscosity of 5 to 100 mPa·s at 25° C., and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or mixtures of octyldodecanol, acetylated lanolin alcohol, cetyl acetate, isododecanol, polyglyceryl-3-diisostearate, or mixtures thereof. The high viscosity surface oils generally have a viscosity of 200-1,000,000 mPa·s at 25° C., preferably a viscosity of 100,000-250,000 mPa·s. Surface oils include castor oil, lanolin and lanolin derivatives, triisocetyl citrate, sorbitan sesquioleate, C10-18 triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or mixtures thereof. Mention may be made, among the optional other non-silicone fatty substances, of mineral oils, such as liquid paraffin or liquid petroleum, of animal oils, such as perhydrosqualene or arara oil, or alternatively of vegetable oils, such as sweet almond, calophyllum, palm, castor, avocado, jojaba, olive or cereal germ oil. It is also possible to use esters of lanolic acid, of oleic acid, of lauric acid, of stearic acid or of myristic acid, for example; alcohols, such as oleyl alcohol, linoleyl or linolenyl alcohol, isostearyl alcohol or octyldodecanol; or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

The order of mixing components A), B), and C) is not critical, but typically A) and B) are first mixed and then water added to the mixture. There are no special requirements or conditions needed for effecting the mixing of components A), B), and C). The mixing can be conducted in a batch, semi-continuous, or continuous process.

The amount of components A), B), and C) can vary in the process, but typically range as follows;

A) 2 to 50 wt %, alternatively 2 to 25 wt %, or alternatively 2 to 15 wt %,

B) 0 to 50 wt %, alternatively 2 to 25 wt %, or alternatively 2 to 15 wt %,

C) 0 to 50 wt %, alternatively 1 to 20 wt %, or alternatively 2 to 10 wt %, and sufficient amount of water to provide the sum of the wt % of A), B), and C) and water content to equal 100%.

In one embodiment of the present invention, the dispersed particles containing the siloxane resin A) form vesicles in aqueous compositions. Thus, the present invention also relates to a process for making a vesicle composition comprising;

I) mixing,
   A) the siloxane resin as described in Formula I above,
   B) an optional water miscible volatile solvent,
   C) optionally, an organic or silicone oil,
   with water to form an aqueous dispersion of the siloxane resin,
II) optionally, removing the water miscible volatile solvent from the aqueous dispersion to form the vesicle composition.

In this embodiment, the optional components B) and C) are as described above, and mixing techniques the same.

The formation of vesicles in the compositions of the present invention can be confirmed by techniques common in the state of the art. Typically, vesicles having a lamellar phase structure which exhibit birefringence when examined with a cross polarizing microscope. Alternatively, the formation of vesicles can be demonstrated by Cyro-Transmission Electron Microscopy (Cryo-TEM) techniques. Particle size measurements can also be used to indicate that the organopolysiloxanes are sufficiently dispersed in aqueous medium typical of vesicle sizes For example, average particle sizes of less than 0.500 μm (micrometers), are typical for dispersed vesicles. Vesicles having an average particle size of less than 0.200 μm, or 0.100 μm are possible with the teachings of the present invention.

The present invention also relates to the aqueous compositions of the siloxane resins, as described above, further comprising a personal, household, or health care ingredient. Thus, the aqueous dispersions and vesicle compositions can be used to entrap, and subsequently deliver after application, a personal, household care, or health care ingredient. A listing of possible personal, household, or health care ingredients is taught in WO 03/101412, which is incorporated herein by reference. The personal or health care ingredient can also be selected from a personal or health care "active", that is, any compound known to have either cosmetic and/or pharmaceutical activity. A representative listing of such personal or health care actives is disclosed in U.S. Pat. No. 6,168,782, which is hereby incorporated by reference.

EXAMPLES

These examples are intended to illustrate the invention to one of ordinary skill in the art and should not be interpreted as limiting the scope of the invention set forth in the claims.

Example 1

Reference

Preparation of Polyether-Functional $M_xM^{PE}_yT^{Pr}_z$ Resins

Several polyether-functional siloxane resins were prepared having the average formula $M_xM^{PE}_yT^{Pr}_z$; wherein Pr represents the propyl group and PE represents a polyether group. The average formula for each and other structural characteristics are summarized in Table 1.

TABLE 1

| Example | Structure | M fraction | M' fraction | $T^{Pr}$ fraction | $(M + T^{Pr})/M'$ | Mw | Wt % silicone |
|---|---|---|---|---|---|---|---|
| 1A | $M'_{0.68}T^{Pr}_{0.31}$ | 0 | 0.68 | 0.31 | 0.46 | 4208 | 22.0 |
| 1B | $M'_{0.18}T^{Pr}_{0.82}$ | 0 | 0.018 | 0.82 | 4.56 | 22714 | 50.2 |
| 1C | $M_xM'_yT^{Pr}_z$ | 0.13 | 0.11 | 0.75 | 8.00 | 15306 | 61.3 |
| 1D | $M_xM'_yT^{Pr}_z$ | 0.13 | 0.11 | 0.75 | 8.00 | 29206 | 61.3 |
| 1E | $M_xM'_yT^{Pr}_z$ | 0.135 | 0.035 | 0.82 | 27.29 | 12401 | 83.1 |

The general procedure for preparing polyether-functional $MM'T^{Pr}$ resins as shown in Table 1 is described for 1C. The starting SiH functional resin with desired structure was synthesized by FC24 catalyzed capping of DC-8004 $T^{Pr}$ resin intermediate with EBB end-blocker and DC 3-7010 (SiH dimer). The finished SiH functional $M_xM'_yT^{Pr}_z$ resin had a 71.33 w/w % non-volatile content (NVC) in toluene and 0.124 w/w % SiH.

A reaction kettle was charged with 59.2 g of Polyglycol AE501 monoallyloxy polyether (obtained from Dow Chemical, having 3.14 w/w % OH, 4.81 w/w % Vi), 0.1 g sodium acetate, 53.7 g of isopropyl alcohol and 100 g of the SiH functional resin. After heating to 70° C., 4.5 ppm equivalent of Pt catalyst was then added to initiate the reaction. After allowing the reaction to proceed for 2 hours, the resulting reaction mixture was filtered and stripped of volatiles by heating at reduced pressure.

Example 2

Dispersions of a $MM'T^{Pr}$-PEO Resin and Effect of Adding Volatile Solvent

Aqueous dispersions of the siloxane resin of Example 1C were prepared according to the formulations and procedures as described in Table 2. Example 2A shows that when a dispersion was attempted with just the resin alone (no volatile solvent such as isopropanol present), the resin separated from the aqueous phase and no stable dispersion was observed. However, the polyether-functional $MM'T^{Pr}$ resin, $MM'T^{Pr}$-PEO resin, was successfully dispersed in water containing various amounts of isopropanol, as shown by Examples 2B, 2C, and 2D in Table 2.

TABLE 2

| | Example # | | | |
|---|---|---|---|---|
| | 2A | 2B | 2C | 2D |
| MM'T$^{Pr}$-PEO resin, g | 2.004 | 2.077 | 2.081 | 2.016 |
| Isopropanol, g | | 4.018 | 6.000 | 8.029 |
| De-ionized water, g | 18.024 | 14.000 | 12.079 | 10.242 |
| Wt. % SPE resin | 10.01 | 10.34 | 10.32 | 9.94 |
| Wt. % IPA | 0.00 | 20.00 | 29.76 | 39.58 |
| Wt. % Water | 89.99 | 69.67 | 59.92 | 59.49 |
| Rate of Dispersion | No dispersion | Moderate | Fast | Fast |
| Dispersion appearance | Separated resin in water | Hazy, uniform dispersion | Clear, uniform dispersion | Clear, uniform dispersion |
| Average particle size, um | n/a | 0.106 | 0.025 | 0.037 |
| D(v, 0.5), um | | 0.022 | 0.023 | 0.026 |
| D(v, 0.9), um | | 0.036 | 0.036 | 0.038 |
| Peak 1, diameter, um | | 0.022 | 0.023 | 0.026 |
| Peak 1, volume % | | 0.950 | 1.000 | 0.980 |
| Peak 2, diameter, um | | 0.596 | | 0.753 |
| Peak 2, volume % | | 2% | | 2% |
| Peak 3, diameter, um | | 3.35 | | |
| Peak 3, volume % | | 3% | | |

Example 3

Dispersions of Neat and Vitamin Loaded Vesicles

Polyether-functional MM'T$^{Pr}$-PEO resins of different wt. % silicone contents were used to prepare neat aqueous vesicle dispersions and also for the entrapment of oil-soluble actives in the formed vesicles. Table 3 summarizes the vesicles compositions and vitamin A palmitate (VAP) entrapped vesicles dispersions prepared from several of the MM'T$^{Pr}$-PEO resins as prepared from Example 1. The actives entrapped vesicles were stable in water.

TABLE 3

Dispersion of Neat and VAP Loaded MM'T$^{Pr}$-PEO Resins

| Resin ID | 1B | 1D | 1E |
|---|---|---|---|
| SiH Resin Structure | M'$_{0.18}$T$^{PR}_{0.82}$ | M$_{0.13}$M'$_{0.11}$T$^{PR}_{0.75}$ | M$_{0.135}$M'$_{0.035}$T$^{PR}_{0.82}$ |
| Wt. % Silicone | 50.2 | 61.3 | 83.1 |
| Neat Dispersions: stripped | | 3A | 3B |

TABLE 3-continued

Dispersion of Neat and VAP Loaded MM'T$^{Pr}$-PEO Resins

| Resin ID | 1B | 1D | 1E |
|---|---|---|---|
| VAP loaded SPE: homogenized only | 3C | 3D | 3E |
| VAP loaded SPE: homogenized, stripped | 3F | 3G | |

Example 4

Vesicle Dispersions from MM'T$^{Pr}$-PEO Resin Having High Wt. % Silicone

M$_{0.135}$M'$_{0.035}$T$^{Pr}_{0.82}$-PEO resin (1E) was first dispersed in IPA/water medium and particles with average size of 0.0321 was found in Example 4A (in 30 IPA/60 water mixture) and 0.0040 μm in 4C (in 44 IPA/46 w/w water mixture).

Example 4B dispersion was prepared by stripping off isopropanol from 4A dispersion to give a final composition of 15 silicone polyether vesicles in 4 IPA/81 water. The vesicles have average particle size of 0.028 μm.

| | Example # | | |
|---|---|---|---|
| | 4A | 4B | 4C |
| Process History | Mechanically mixed | Mixed, Rotovap stripped | Mechanically mixed |
| 19002-122 MM'T$^{Pr}$-PEO resin, g | 20.16 | 19.09 | 0.500 |
| Isopropanol, g | 60.26 | 51.34 | 2.274 |
| De-ionized water, g | 121.00 | 103.10 | 2.375 |
| Batch before strip | 201.42 | 171.62 | 5.149 |
| Volatile solvent stripped, g | | 46.17 | |
| Batch after strip, g | 201.42 | 125.45 | 5.15 |

-continued

| | Example # | | |
|---|---|---|---|
| | 4A | 4B | 4C |
| Wt. % SPE | 11.12 | 14.99 | 9.71 |
| Wt. % IPA | 29.92 | 4.06 | 44.16 |
| Wt. % Water | 60.07 | 80.95 | 46.13 |
| Appearance | Clear | Slightly hazy | Almost clear, |
| Average size, um | 0.0321 | 0.0282 | 0.0040 |
| D(v, 0.5), um | 0.0225 | 0.0261 | 0.0034 |
| D(v, 0.9), um | 0.0427 | 0.0420 | 0.0058 |
| Peak 1, diameter | 0.0221 | 0.0261 | 0.0034 |
| Peak 1, volume % | 96% | 100% | 100% |
| Peak 2, diameter | 0.2374 | | |
| Peak 2, volume % | 4% | | |

Example 5

Dispersion of $M_{0.135}M'_{0.035}T^{Pr}_{0.82}$-PEO Resin Havnig 61.3% Silicone Dispersions of $M_{0.135}M'_{0.035}T^{Pr}_{0.82}$-PEO resin were prepared using the procedure of Example 4. The polyether-functional $M_{0.135}M'_{0.035}T^{Pr}_{0.82}$-PEO resin contains about 61.3 wt. % silicone and does not readily disperse in water. As detailed in the Table 4, $M_{0.135}M'_{0.035}T^{Pr}_{0.82}$-PEO resin was dispersed in an isopropanol/water mixture of 30/60 w/w. The dispersion had a particle size of 0.026 um. Dispersions of the $M_{0.135}M'_{0.035}T^{Pr}_{0.82}$-PEO resin in pure water were obtained by subsequently stripped off isopropanol. Dispersions of two particle size ranges are obtained: 0.344 um and 2.03 um.

| | ID example | |
|---|---|---|
| | 5A | 5B |
| Process History | Mechanically mixed | Mixed, Rotovap stripped |
| 18817-57 MM'$T^{Pr}$-PEO resin, g | 30.0 | 30.0 |
| IPA, g | 90.0 | |
| Water, g | 180.0 | 180.0 |
| Wt. % SPE | 10.0 | 14.3 |
| Wt. % IPA | 30.0 | 0.0 |
| Wt. % Water | 60.0 | 85.7 |
| Appearance | water-white clear dispersion | Milky dispersion of vesicles with a bimodal size profiles; separated into 2 layers |
| Average particle size, um | 0.02606 | 2.051 |
| D(v, 0.5), um | 0.02395 | 1.954 |
| D9v, 0.9), um | 0.0384 | 3.38 |
| Peak 1, diameter, um | 0.02395 | 0.344 |
| Peak 1, volume % | 100% | 7% |
| Peak 2, diameter, um | | 2.029 |
| Peak 2, volume % | | 93% |

Example 5B dispersion separated into 2-layers: a slightly hazy top layer and a milky bottom layer. Further analysis of the respectively layers showed the top layer is the dispersion of small particles, and the bottom layer the dispersion of larger particles.

Cryo-TEM image was sought after for the top layer of 5B dispersion of the $M_{0.135}M'_{0.035}T^{Pr}_{0.82}$-PEO resin, as shown FIG. 1 below. The cryo-TEM image confirmed the particles in the dispersion are vesicles, primarily unilamellar small vesicles.

The invention claimed is:

1. An aqueous composition having dispersed particles wherein the dispersed particles have an average particle size of less than 10 micrometers and comprise a siloxane resin comprising at least 80 mole % of siloxy units having the formula $(R^1{}_2R'SiO_{1/2})_x(R''SiO_{3/2})_y$, wherein x and y have a value of 0.1 to 0.95, $R^1$ is an alkyl or aryl group having from 1 to 8 carbon atoms, R' is a monovalent organic group containing polyoxyalkylene units, R'' is a monovalent hydrocarbon group having 2 to 8 carbon atoms.

2. The composition of claim 1 wherein the siloxane resin comprises the units:

$(R^1{}_3SiO_{1/2})_a$     (i)

$(R^2{}_2SiO_{2/2})_b$     (ii)

$(R^3SiO_{3/2})_c$,     (iii)

$(SiO_{4/2})_d$,     (iv)

$(R^1_2R'SiO_{1/2})_x$ and (v)

$(R''SiO_{3/2})_y$, (vi)

wherein $R^1$, $R^2$, and $R^3$ are independently an alkyl group having from 1 to 8 carbon atoms, an aryl group, a carbinol group, or an amino group, R' is a monovalent polyoxyalkylene group, R" is a monovalent hydrocarbon group having 2 to 8 carbon atoms a, b, c, and d have value of zero to 0.2, x and y have a value of 0.1 to 0.95, with the provisos that the value of x+y is equal to or greater than 0.80, and the value of a+b+c+d+x+y=1.

3. The composition of claim 1 where R' is a propyl group.

4. The composition of claim 1 wherein R' has the formula —$R^4O(C_nH_{2n}O)_zR^5$, wherein n is from 2 to 4 inclusive, z is greater than 4, $R^4$ is a divalent hydrocarbon containing 2 to 8 carbon atoms, $R^5$ is hydrogen, an acetyl group, or a monovalent hydrocarbon containing 1 to 8 carbons.

5. The composition of claim 4 wherein n is 2, z is 4 to 24, $R^4$ is propylene, $R^5$ is hydrogen.

6. The aqueous composition of claim 1 further comprising a water miscible volatile solvent.

7. The aqueous composition of claim 6 where the solvent is an alcohol.

8. The aqueous composition of claim 1 wherein the dispersed particles are vesicles.

9. The aqueous composition of claim 8 wherein the vesicles further comprise a non-aqueous component.

10. A process for preparing an aqueous dispersion comprising

I) mixing

A) a siloxane resin comprising at least 80 mole % of siloxy units having the formula $(R^1_2R'SiO_{1/2})_x(R''SiO_{3/2})$, wherein x and y have a value of 0.1 to 0.95, $R^1$ is an alkyl or aryl group having from 1 to 8 carbon atoms, R' is a monovalent organic group containing polyoxyalkylene units, R" is a monovalent hydrocarbon group having 2 to 8 carbon atoms B) optionally, a water miscible volatile solvent, C) optionally, an organic or silicone oil, with water to form an aqueous dispersion of the siloxane resin, II) removing the water miscible volatile solvent from the aqueous dispersion.

11. The process of claim 10 wherein C) a silicone or organic oil is included in the mixing of step I).

12. The process of claim 11 wherein the silicone oil is a volatile methyl siloxane.

13. A process for making a vesicle composition comprising;

I) mixing,

A) a siloxane resin comprising at least 80 mole % of siloxy units having the formula $(R^1_2R'SiO_{1/2})_x(R''SiO_{3/2})_y$, wherein x and y have a value of 0.1 to 0.95, $R^1$ is an alkyl or aryl group having from 1 to 8 carbon atoms, R' is a monovalent organic group containing polyoxyalkylene units, R" is a monovalent hydrocarbon group having 2 to 8 carbon atoms, B) an optional a water miscible volatile solvent, C) optionally, an organic or silicone oil, with water to form an aqueous dispersion of the siloxane resin, II) removing the water miscible volatile solvent from the aqueous dispersion to form the vesicle composition.

14. The vesicle composition produced by the process of claim 13.

15. The aqueous composition of claim 1 further comprising a personal, household, or healthcare active ingredient.

16. A personal, household, and healthcare composition comprising the aqueous composition of claim 1.

17. The vesicle composition of claim 8 further comprising a personal, household, or healthcare active ingredient.

18. A personal, household, and healthcare composition comprising the vesicle composition of claim 8.

* * * * *